(12) United States Patent
Topolkaraev et al.

(10) Patent No.: US 9,205,152 B2
(45) Date of Patent: *Dec. 8, 2015

(54) MELT-BLENDED PROTEIN COMPOSITION

(71) Applicant: Kimberly-Clark Worldwide, Inc., Neenah, WI (US)

(72) Inventors: Vasily A. Topolkaraev, Appleton, WI (US); Neil T. Scholl, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 36 days.

This patent is subject to a terminal disclaimer.

(21) Appl. No.: 13/863,525

(22) Filed: Apr. 16, 2013

(65) Prior Publication Data

US 2013/0224316 A1    Aug. 29, 2013

Related U.S. Application Data

(62) Division of application No. 12/961,625, filed on Dec. 7, 2010, now Pat. No. 8,445,032.

(51) Int. Cl.
| | |
|---|---|
| *A61K 36/00* | (2006.01) |
| *A61K 47/00* | (2006.01) |
| *A61K 31/05* | (2006.01) |
| *B29C 47/00* | (2006.01) |
| *A61K 47/42* | (2006.01) |
| *A61K 8/02* | (2006.01) |
| *A61K 8/64* | (2006.01) |
| *A61Q 17/00* | (2006.01) |
| *A61Q 19/10* | (2006.01) |
| *A01N 25/28* | (2006.01) |
| *C08K 5/00* | (2006.01) |
| *C08K 5/053* | (2006.01) |
| *C08L 89/00* | (2006.01) |
| *C08K 5/09* | (2006.01) |
| *C08K 5/1515* | (2006.01) |

(52) U.S. Cl.
CPC .............. *A61K 47/42* (2013.01); *A01N 25/28* (2013.01); *A61K 8/0208* (2013.01); *A61K 8/645* (2013.01); *A61Q 17/005* (2013.01); *A61Q 19/10* (2013.01); *C08K 5/0016* (2013.01); *C08K 5/0025* (2013.01); *C08K 5/053* (2013.01); *C08K 5/09* (2013.01); *C08K 5/1515* (2013.01); *C08L 89/00* (2013.01)

(58) Field of Classification Search
None
See application file for complete search history.

(56) References Cited

U.S. PATENT DOCUMENTS

| | | |
|---|---|---|
| 3,351,531 A | 11/1967 | Noznick et al. |
| 3,354,506 A | 11/1967 | Raley |
| 3,494,821 A | 2/1970 | Evans |
| 3,650,649 A | 3/1972 | Schippers |
| 3,801,429 A | 4/1974 | Schrenk et al. |
| 3,973,695 A | 8/1976 | Ames |
| 4,100,324 A | 7/1978 | Anderson et al. |
| 4,144,370 A | 3/1979 | Boulton |
| 4,652,441 A | 3/1987 | Okada et al. |
| 4,690,825 A | 9/1987 | Won |
| 4,695,450 A | 9/1987 | Bauer et al. |
| 4,820,435 A | 4/1989 | Zafiroglu |
| 5,023,080 A | 6/1991 | Gupta |
| 5,057,361 A | 10/1991 | Sayovitz et al. |
| 5,179,164 A | 1/1993 | Lausberg et al. |
| 5,240,764 A | 8/1993 | Haid et al. |
| 5,284,703 A | 2/1994 | Everhart et al. |
| 5,320,669 A | 6/1994 | Lim et al. |
| 5,330,768 A | 7/1994 | Park et al. |
| 5,350,624 A | 9/1994 | Georger et al. |
| 5,354,726 A | 10/1994 | Narayanan et al. |
| 5,395,055 A | 3/1995 | Shutov et al. |
| 5,397,834 A | 3/1995 | Jane et al. |
| 5,421,898 A | 6/1995 | Cavanagh |
| 5,523,293 A | 6/1996 | Jane et al. |
| 5,589,195 A | 12/1996 | Potter |
| 5,665,428 A | 9/1997 | Cha et al. |

(Continued)

FOREIGN PATENT DOCUMENTS

| | | | |
|---|---|---|---|
| EP | 0388718 A2 | 9/1990 | |
| EP | 0388718 A3 | 9/1990 | |

(Continued)

OTHER PUBLICATIONS

Article—Ryan et al., "Conjugation of salmon calcitonin to a combed-shaped end functionalized poly(poly (ethylene glycol) methyl ether methacrylate) yields a bioactive stable conjugate," *Journal of Controlled Release*, vol. 135, 2009, pp. 51-59.

(Continued)

*Primary Examiner* — Chris R Tate
*Assistant Examiner* — Russell Fiebig
(74) *Attorney, Agent, or Firm* — Dority & Manning, P.A.

(57) ABSTRACT

A melt-processed protein composition formed from a protein, plasticizer, and an electrophilic reagent is provided. The electrophilic reagent, for instance, may be selected to undergo a nucleophilic addition reaction with free sulfhydryl and/or thiyl radicals to help minimize the formation of disulfide crosslinking bonds that could otherwise lead to protein aggregation during melt processing. To enhance the degree to which the electrophilic reagent can limit crosslinking, a plasticizer is also employed that helps to mediate the adsorption of the electrophilic reagent into the internal structure of the protein, where it can be more stably retained. Furthermore, the temperature and shear rate employed during melt blending may also be selected to be relatively low to help limit polypeptide dissociation, thereby minimizing the impact of aggregation and embrittlement.

10 Claims, 1 Drawing Sheet

(56) References Cited

U.S. PATENT DOCUMENTS

| | | | |
|---|---|---|---|
| 5,687,875 A | 11/1997 | Watts et al. | |
| 5,702,717 A | 12/1997 | Cha et al. | |
| 5,723,588 A | 3/1998 | Donofrio et al. | |
| 5,735,588 A | 4/1998 | Dittman et al. | |
| 5,747,162 A * | 5/1998 | Temple et al. | 428/395 |
| 5,785,179 A | 7/1998 | Buczwinski et al. | |
| 5,824,732 A | 10/1998 | Jablon | |
| 5,871,872 A | 2/1999 | Matijevic et al. | |
| 5,919,471 A | 7/1999 | Saferstein et al. | |
| 5,922,379 A * | 7/1999 | Wang | 426/138 |
| 5,928,661 A | 7/1999 | Fujita et al. | |
| 5,964,351 A | 10/1999 | Zander | |
| 6,030,331 A | 2/2000 | Zander | |
| 6,090,925 A | 7/2000 | Woiszwillo et al. | |
| 6,121,165 A | 9/2000 | Mackey et al. | |
| 6,133,166 A | 10/2000 | Nissing et al. | |
| 6,158,614 A | 12/2000 | Haines et al. | |
| 6,269,969 B1 | 8/2001 | Huang et al. | |
| 6,269,970 B1 | 8/2001 | Huang et al. | |
| 6,270,878 B1 | 8/2001 | Wegele et al. | |
| 6,273,359 B1 | 8/2001 | Newman et al. | |
| 6,315,864 B2 | 11/2001 | Anderson et al. | |
| 6,523,690 B1 | 2/2003 | Buck et al. | |
| 6,568,625 B2 | 5/2003 | Faulks et al. | |
| 6,589,549 B2 | 7/2003 | Shih et al. | |
| 6,719,995 B2 | 4/2004 | Rajaiah et al. | |
| 6,766,919 B2 | 7/2004 | Huang et al. | |
| 6,770,433 B2 | 8/2004 | Hioki | |
| 6,806,213 B2 | 10/2004 | Brooks | |
| 6,806,353 B2 | 10/2004 | Zhang et al. | |
| 6,824,734 B2 | 11/2004 | Boggs et al. | |
| 6,989,149 B2 | 1/2006 | Glenn, Jr. et al. | |
| 7,127,771 B2 | 10/2006 | McDevitt et al. | |
| 7,250,152 B2 | 7/2007 | Gentile et al. | |
| 7,338,927 B2 | 3/2008 | Shapiro | |
| 7,452,592 B2 | 11/2008 | Cowton | |
| 7,462,348 B2 | 12/2008 | Gruenbacher et al. | |
| 7,560,422 B2 | 7/2009 | Shapiro | |
| 7,605,096 B2 | 10/2009 | Tomarchio et al. | |
| 7,612,029 B2 | 11/2009 | Foland et al. | |
| 7,614,812 B2 | 11/2009 | Reddy et al. | |
| 7,662,409 B2 | 2/2010 | Masters | |
| 7,803,413 B2 | 9/2010 | van Lengerich et al. | |
| 7,803,414 B2 | 9/2010 | van Lengerich et al. | |
| 2003/0031722 A1 | 2/2003 | Cao et al. | |
| 2003/0082219 A1 | 5/2003 | Warren et al. | |
| 2003/0105207 A1 | 6/2003 | Kleyer et al. | |
| 2003/0135172 A1 | 7/2003 | Whitmore et al. | |
| 2004/0018241 A1 | 1/2004 | Houze et al. | |
| 2004/0026289 A1 | 2/2004 | Halkyard | |
| 2004/0037870 A9 | 2/2004 | Fotinos | |
| 2004/0043134 A1 * | 3/2004 | Corriveau et al. | 426/658 |
| 2004/0234609 A1 | 11/2004 | Collier et al. | |
| 2004/0255408 A1 | 12/2004 | Norton et al. | |
| 2005/0048121 A1 | 3/2005 | East et al. | |
| 2005/0158369 A1 | 7/2005 | Dorschner et al. | |
| 2005/0214349 A1 | 9/2005 | Nie et al. | |
| 2005/0238591 A1 | 10/2005 | Sagel et al. | |
| 2005/0245162 A1 | 11/2005 | McCormack et al. | |
| 2006/0062832 A1 | 3/2006 | Lopes | |
| 2006/0128248 A1 | 6/2006 | Ellis | |
| 2007/0224261 A1 | 9/2007 | Draper | |
| 2007/0254035 A1 | 11/2007 | Hao et al. | |
| 2007/0256247 A1 | 11/2007 | Privitera et al. | |
| 2007/0269567 A1 | 11/2007 | McMindes et al. | |
| 2008/0160084 A1 | 7/2008 | Huynh et al. | |
| 2008/0200359 A1 | 8/2008 | Smets et al. | |
| 2008/0207481 A1 | 8/2008 | Meine et al. | |
| 2008/0221003 A1 | 9/2008 | Meine et al. | |
| 2009/0136555 A1 | 5/2009 | Crowley et al. | |
| 2009/0175806 A1 | 7/2009 | Modak et al. | |
| 2009/0186096 A1 | 7/2009 | Kritzman et al. | |
| 2009/0196909 A1 | 8/2009 | Cooper et al. | |
| 2009/0226530 A1 | 9/2009 | Lassner et al. | |
| 2009/0232905 A1 | 9/2009 | Weiss et al. | |
| 2009/0286437 A1 | 11/2009 | Cunningham et al. | |
| 2009/0297664 A1 | 12/2009 | Forte et al. | |
| 2010/0034907 A1 | 2/2010 | Daigle et al. | |
| 2010/0065445 A1 | 3/2010 | Stevenson | |
| 2010/0101605 A1 | 4/2010 | Saint Victor | |
| 2010/0136201 A1 | 6/2010 | Bigeard et al. | |
| 2010/0144584 A1 | 6/2010 | Saint Victor | |
| 2010/0159170 A1 | 6/2010 | Wang et al. | |
| 2010/0159777 A1 | 6/2010 | Wang et al. | |
| 2010/0234517 A1 | 9/2010 | Plantenberg et al. | |
| 2010/0240724 A1 | 9/2010 | Chang et al. | |
| 2010/0240799 A1 | 9/2010 | Hofmann et al. | |
| 2010/0247371 A1 | 9/2010 | Farrugia et al. | |
| 2010/0272831 A1 | 10/2010 | Lagaron-Cabello et al. | |
| 2010/0272940 A1 | 10/2010 | Shi et al. | |
| 2011/0086084 A1 | 4/2011 | Koenig et al. | |
| 2011/0086085 A1 | 4/2011 | Wenzel et al. | |
| 2011/0150955 A1 | 6/2011 | Klingman | |
| 2012/0141566 A1 | 6/2012 | Topolkaraev et al. | |
| 2012/0141567 A1 | 6/2012 | Wang et al. | |
| 2012/0141569 A1 | 6/2012 | Lee et al. | |
| 2012/0141571 A1 | 6/2012 | Lee et al. | |

FOREIGN PATENT DOCUMENTS

| | | |
|---|---|---|
| EP | 0504387 B1 | 7/1995 |
| EP | 0863942 B1 | 9/1998 |
| EP | 1004703 A1 | 5/2000 |
| EP | 1023863 A1 | 8/2000 |
| EP | 1059032 A1 | 12/2000 |
| EP | 1059378 A1 | 12/2000 |
| EP | 1275370 A1 | 1/2003 |
| EP | 1275371 A1 | 1/2003 |
| EP | 1624013 A1 | 2/2006 |
| EP | 1618240 B1 | 8/2006 |
| EP | 1408926 B1 | 1/2007 |
| EP | 1757261 A2 | 2/2007 |
| EP | 1757261 A3 | 2/2007 |
| EP | 1867317 A2 | 12/2007 |
| EP | 1867317 A3 | 12/2007 |
| FR | 2900940 A1 | 11/2007 |
| GB | 2444112 A | 5/2008 |
| WO | WO 9003784 A1 | 4/1990 |
| WO | WO 9205708 A1 | 4/1992 |
| WO | WO 0151557 A1 | 7/2001 |
| WO | WO 02074430 A1 | 9/2002 |
| WO | WO 2006000032 A1 | 1/2006 |
| WO | WO 2007135273 A2 | 11/2007 |
| WO | WO 2007135273 A3 | 11/2007 |
| WO | WO 2008030969 A2 | 3/2008 |
| WO | WO 2008030969 A3 | 3/2008 |
| WO | WO 2008006388 A1 | 5/2008 |
| WO | WO 2008006388 A8 | 5/2008 |
| WO | WO 2008149232 A2 | 12/2008 |
| WO | WO 2008149232 A3 | 12/2008 |
| WO | WO 2009118665 A2 | 10/2009 |
| WO | WO 2009118665 A3 | 10/2009 |
| WO | WO 2009155115 A2 | 12/2009 |
| WO | WO 2009155115 A3 | 12/2009 |
| WO | WO 2010022353 A1 | 2/2010 |
| WO | WO 2010030234 A1 | 3/2010 |
| WO | WO 2010070469 A2 | 6/2010 |
| WO | WO 2010070469 A3 | 6/2010 |
| WO | WO 2010070470 A2 | 6/2010 |
| WO | WO 2010070470 A3 | 6/2010 |

OTHER PUBLICATIONS

Supplementary European Search Report, Jun. 6, 2014, 10 pages.
Article—Auvergne et al., "Reactivity of Wheat Gluten Protein during Mechanical Mixing: Radical and Nucleophilic Reactions for the Addition of Molecules on Sulfur," *Biomacromolecules*, vol. 9, No. 2, 2008, pp. 664-671.
Article—Camire, Mary Ellen, "Protein Functionality Modification by Extrusion Cooking," *JAOCS*, vol. 68, No. 3, Mar. 1991, pp. 200-205 (Presented at the 81$^{st}$ AOCS Annual Meeting, Baltimore, 1990).
Article—Hu et al., "Evaluation of the environmental fate of thymol and phenethyl Propionate in the laboratory," *Pest Management Science*, vol. 64, Issue 7, Jul. 2008, pp. 775-779.

(56) References Cited

OTHER PUBLICATIONS

Article—Kurniawan et al., "Chemical Modification of Wheat Protein-Based Natural Polymers: Grafting and Cross-Linking Reactions with Poly(ethylene oxide) Diglycidyl Ether and Ethyl Diamine," *Biomacromolecules*, vol. 8, No. 9, 2007, pp. 2909-2915.
Article—Lawton et al, "High-Temperature Short-Time Extrusion of Wheat Gluten and a Bran-Like Fraction," *Cereal Chem.*, vol. 62, No. 4, 1985, pp. 267-271.
Article—Liu et al., "Modifications of Soy Protein Plastic with Functional Monomer with Reactive Extrusion," *J. Polym. Environ.*, vol. 16, No. 3, 2008, pp. 177-182.
Article—Mastromatteo et al., "Controlled release of thymol from zein based film," *Innovative Food Science and Emerging Technologies*, vol. 10, 2009, pp. 222-227.
Article—Nobile et al., "Active packaging by extrusion processing of recyclable and biodegradable polymers," *Journal of Food Engineering*, vol. 93, 2009, pp. 1-6.
Article—Nobile et al., "Antimicrobial efficacy and release kinetics of thymol from zein films," *Journal of Food Engineering*, vol. 89, 2008, pp. 57-63.
Article—O'Lenick, Jr., Anthony J., "Silicone Emulsions and Surfactants—A Review," *Silicone Spectator*, May 2000, 18 pages.
Article—Parris, et al., "Encapsulation of Essential Oils in Zein Nanosphericai Particles," *J. Agric. Food Chem.*, vol. 53, No. 12, Jun. 15, 2005, pp. 4788-4792.
Article—Redl et al., "Extrusion of Wheat Gluten Plasticized with Glycerol: Influence of Process Conditions on Flow Behavior, Rheological Properties, and Molecular Size Distribution," *Cereal Chem.*, vol. 76, No. 3, 1999, pp. 361-370.
Article—Sanchez-Garcia et al., "Novel Polycaprolactone Nanocomposites Containing Thymol of Interest in Antimicrobial Film and Coating Applications," *Journal of Plastic Film and Sheeting*, vol. 24, Jul.-Oct. 2008, pp. 239-251.
Article—Ullsten et al, "Enlarged Processing Window of Plasticized Wheat Gluten Using Salicylic Acid," *Biomacromolecules*, vol. 7, No. 3, 2006, pp. 771-776.
Article—Vaz et al., "Soy Matrix Drug Delivery Systems Obtained by Melt-Processing Techniques," *Biomacromolecules*, vol. 4, No. 6, Nov./Dec. 2003, pp. 1520-1529.
Article—Verbeek et al., "Extrusion Processing and Properties of Protein-Based Thermoplastics," *Macromolecular Materials and Engineering*, vol. 295, 2010, pp. 10-21.
Paper entitled "Chemistry of Crosslinking" from Thermo Fisher Scientific, Inc., 2010, 8 pages.
Presentation to the Midwest Chapter of the Society of Cosmetic Chemists—The HLB System—A Time Saving Guide to Surfactant Selection, Mar. 9, 2004, by Uniqema, 39 pages.
ASTM D 445-04—Standard Test Method for Kinematic Viscosity of Transparent and Opaque Liquids (and the Calculation of Dynamic Viscosity), Current edition approved May 1, 2004, originally approved in 1937.
ASTM 5034 95—Standard Test Method for Breaking Strength and Elongation of Textile Fabrics (Grab Test), Current edition approved May 15, 1995.
Search Report and Written Opinion for PCT/IB2011/054838 dated Jun. 28, 2012, 12 pages.
US 5,885,702, 03/1999, Abdel-Malik et al. (withdrawn)

* cited by examiner

Fig. 1

Fig. 2

MELT-BLENDED PROTEIN COMPOSITION

RELATED APPLICATIONS

The present application is a divisional of U.S. application Ser. No. 12/961,625, filed on Dec. 7, 2010, which is incorporated herein in its entirety by reference thereto.

BACKGROUND OF THE INVENTION

Proteins are often employed to encapsulate a component so that it can be released over a period of time. For example, an article entitled *"Encapsulation of Essential Oils in Zein Nanospherical Particles"* (Parris, et al., *J. Agric. Food Chem.* 2005, 53, 4788-4792) broadly describes the encapsulation of thymol in zein nanospheres by mixing the oil with zein particles in the presence of a solvent (e.g., ethanol). The particles are said to be useful for oral or injectable administration of biological materials into the body. Another article entitled *"Controlled Release of Thymol from Zein Based Film"* (Mastromatteo, et al., *J. Innovative Food and Emerging Technologies* 2009, 10, 222-227) broadly describes films formed by dissolving corn zein and glycerol into ethanol, and thereafter adding thymol to form a solution. The solution is poured into a Petri dish and dried to form the film.

One problem with the techniques described above is that they generally rely on solvents (e.g., ethanol) to help dissolve the oil into a solution. A disadvantage of the use of solvents is that both the oil and protein must be soluble in a common solvent system, which puts a limit on what type of components may be employed in the composition. Also, solvent-based solutions require a substantial amount of time, energy, and material for processing. Still further, a portion of the oil may escape from the solution when the solvent is evaporated, which requires the use of a greater amount of the oil than would normally be needed. Notwithstanding the above, the ability to use a "solventless" process is complicated by the tendency of proteins to lose their flow properties when exposed to the intense shear and elevated temperature normally associated with melt processing. For example, proteins may undergo a conformational change ("denaturation") that causes disulfide bonds in the polypeptide to dissociate into sulfhydryl groups or thiyl radicals. Sulfhydryl groups form when disulfide bonds are chemically reduced while mechanical scission of disulfide bonds causes thiyl radicals to form. Once dissociated, however, free sulfhydryl groups randomly re-associate with other sulfhydryl groups to form new disulfide bond between polypeptides. Thiyl radicals can also randomly re-associate with other thiyl radicals forming new disulfide bonds or thiyl radicals can react with other amino acid functionality creating new forms of cross-linking between polypeptides. Because one polypeptide contains multiple thiol groups, random cross-linking between polypeptide leads to formation of an "aggregated" polypeptide network, which is relatively brittle and leads to a loss of flow properties.

As such, a need currently exists for a protein composition that can be readily melt extruded.

SUMMARY OF THE INVENTION

In accordance with one embodiment of the present invention, a method for forming a protein composition is disclosed that comprises dispersively blending a protein, plasticizer, and electrophilic reagent within a melt blending device at a temperature of from about 20° C. to about 100° C. and a shear rate of from about 1 to about 100 Pascal-seconds. Proteins constitute from about 20 wt. % to about 95 wt. % of the composition, and electrophilic reagents are present in the composition in an amount of from about 0.1 wt. % to about 20 wt. %, based on the weight of the proteins.

In accordance with another embodiment of the present invention, a melt-processed composition is disclosed that comprises at least one plant protein in an amount of from about 20 wt. % to about 95 wt. %, at least one plasticizer in amount of from about 20 wt. % to about 80 wt. % based on the weight of the protein, and at least one electrophilic reagent in an amount of from about 0.1 wt. % to about 20 wt. % based on the weight of the protein.

Other features and aspects of the present invention are discussed in greater detail below.

BRIEF DESCRIPTION OF THE FIGURES

A full and enabling disclosure of the present invention, including the best mode thereof, directed to one of ordinary skill in the art, is set forth more particularly in the remainder of the specification, which makes reference to the appended figures in which.

Repeat use of references characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a melt-processed protein composition formed from a protein, plasticizer, and an electrophilic reagent. Despite the problems normally associated with melt processing proteins, the present inventors have discovered that the processing conditions and components may be selectively controlled to allow for the formation of a stable, melt-processed composition that is able to exhibit good mechanical properties. The electrophilic reagent, for instance, may be selected to undergo a nucleophilic addition reaction with free sulfhydryl and/or thiyl radicals to help minimize the formation of disulfide crosslinking bonds that could otherwise lead to protein aggregation during melt processing. To enhance the degree to which the electrophilic reagent can limit crosslinking, a plasticizer is also employed that helps to mediate the adsorption of the electrophilic reagent into the internal structure of the protein, where it can be more stably retained. Furthermore, the temperature and shear rate employed during melt blending may also be selected to be relatively low to help limit polypeptide dissociation, thereby minimizing the impact of aggregation and embrittlement.

Various embodiments of the present invention will now be described in more detail below.

I. Components

A. Protein

Any of a variety of different proteins may generally be melt processed in the composition of the present invention. Examples of suitable proteins include vegetable proteins, dairy proteins, animal proteins, as well as concentrates or isolates thereof. The protein source may be, for instance, milk (e.g., casein or caeseinates), whey, corn (e.g., zein), wheat (e.g., wheat gluten), soy, or other vegetable or animal sources. Plant proteins are particularly suitable for use in the present invention, such as zein, corn gluten, wheat gluten, whey protein, soy protein, etc. Any form of protein may be used, such as isolates, concentrates and flour. For example, soy proteins may be in the form of an isolate containing from about 75 wt. % to about 98 wt. % protein, a concentrate containing from about 50 wt. % to about 75 wt. % protein, or flour containing from about 30 wt. % to about 50 wt. % protein. In certain embodiments, it is desirable to use a protein that is relatively pure, such as those having a protein content of about 75 wt. % or more, and in some cases, about 85 wt. % or more. Gluten proteins, for instance, may be purified by washing away any associated starch to leave a composite of gliadin and glutenin proteins. In one particular embodiment, a vital wheat gluten is employed. Such vital wheat gluten is commercially available as a creamy-tan powder produced from wheat flour by drying freshly washed gluten. For instance, vital wheat gluten can be obtained from Archer Daniels Midland ("ADM") of Decatur, Ill. under the designations WhetPro® 75 or 80. Similarly, purified soy protein isolates may be prepared by alkaline extraction of a defatted meal and acid precipitation, a technique well-known and used routinely in the art. Such purified soy proteins are commercially available from ADM under the designation PRO-FAM®, which typically have a protein content of 90 wt. % or more. Other purified soy protein products are also available from DuPont of Louisville, Ky. under the designation PRO-COTE® and from Central Soya under the designation Promie R.

If desired, the protein may also be modified using techniques known in the art to improver its ability to disperse in an aqueous solution, which may be applied to the composition to release the botanical oil during and/or just prior to use as described in more detail below. Suitable modification techniques may include pH modification, denaturation, hydrolysis, acylation, reduction, oxidation, etc. Just as an example, gluten may sometimes absorb water until it begins to repel excess water. This results in gluten molecules that are associated closely together such that they resist dispersion in aqueous solutions. To counteract this tendency, the protein may be treated with a pH modifier to increase its solubility in aqueous environments. Typically, the pH modifier is a basic reagent that can raise the pH of the protein, thereby causing it to become more soluble in aqueous solutions. Monovalent cation-containing basic reagents (hereafter "monovalent basic reagents") are particularly suitable for use in the present invention. Examples of such monovalent basic reagents include, for instance, alkali metal hydroxides (e.g., sodium hydroxide, ammonium hydroxide, etc.), ammonia, etc. Of course, multivalent reagents, such as alkaline metal hydroxides (e.g., calcium hydroxide) and alkaline metal oxides (e.g., calcium oxide), may also be employed if desired. When employed, the pH modifier may be present in an amount such that the pH of the protein is from about 7 to about 14, and in some embodiments, from about 8 to about 12.

Hydrolysis of the protein material may also improve water solubility, and can be effected by treating the protein with a hydrolytic enzyme. Many enzymes are known in the art which hydrolyze protein materials, including, but not limited to, proteases, pectinases, lactases, and chymotrypsin. Enzyme hydrolysis is effected by adding a sufficient amount of enzyme to an aqueous dispersion of protein material, typically from about 0.1% to about 10% enzyme by weight of the protein material, and treating the enzyme and protein dispersion. After sufficient hydrolysis has occurred the enzyme may be deactivated by heating, and the protein material may be precipitated from the solution by adjusting the pH of the solution to about the isoelectric point of the protein material.

The composition of the present invention typically employs proteins in an amount of from about 20 wt. % to about 95 wt. %, in some embodiments from about 30 wt. % to about 90 wt. %, and in some embodiments, from about 40 wt. % to about 80 wt. %.

B. Electrophilic Reagent

An electrophilic reagent is also employed in the composition of the present invention that is capable of undergoing a nucleophilic addition reaction with free sulfhydryl and/or thiyl radicals, which are strong nucleophiles in the protein normally associated with disulfide crosslinking. For example, the electrophilic reagent may react with free sulfhydryl groups to inhibit the formation of new disulfide crosslinking bonds. In this manner, the electrophilic reagent can serve as a crosslinking inhibitor and limit aggregation of the protein during melt processing. Various electrophilic reagents that undergo reactions with thiols or thiyls may be employed in the present invention. In one embodiment, for example, the electrophilic reagent is an olefinic compound that can undergo a thiol-ene addition reaction (also known as "Michael addition") with thiols or thiyls. Examples of such olefinic electrophiles include, for instance, (meth)acrylates, (meth)acrylamides, maleimides, acrylonitriles, cyanoacrylates, and so forth. Particularly suitable olefinic electrophiles include (meth)acrylates, such as poly(ethylene glycol)acrylate, poly(ethylene glycol)alkyl ether acrylate (e.g., poly(ethylene glycol ethyl ether acrylate)), poly(ethylene glycol) methacrylate, poly(ethylene glycol)alkyl ether methacrylate, acrylic acid, sodium acrylate, 3-hydroxypropyl methacrylate, 2-hydroxyethyl methacrylate, 3-hydroxypropyl acrylate, 2-hydroxyethyl acrylate, 2-bromoethyl methacrylate, 2-chloroethyl methacrylate, 2-iodoethyl methacrylate, 2-bromoethyl acrylate, 2-chloroethyl acrylate, 2-iodoethyl acrylate, glycidyl methacrylate, 2-cyanoethyl acrylate, glycidyl acrylate, 4-nitrophenyl acrylate, pentabromophenyl acrylate, poly (propylene glycol)methacrylates, poly(propylene glycol) acrylates, 2-sulfoethyl acrylate, 2-sulfoethyl methacrylate, 3-sulfopropyl acrylate, 3-sulfopropyl methacrylate, etc., as well as mixtures thereof.

Another suitable electrophilic reagent for use in the composition is an epoxide compound, which can undergo a nucelophilic ring opening reaction with thiol or thiyl groups. In certain cases, the epoxide compound may contain only one epoxy ring per molecule ("monofunctional"), such as t-butyl glycidyl ether, isopropyl glycidyl ether, isobutyl glycidyl ether, 2-ethylhexyl glycidyl ether, glycidyl hexadecyl ether, glycidyl methyl ether, etc., as well as mixtures thereof. Alternatively, the epoxide compound may contain two or more epoxy rings per molecule ("polyfunctional"). When employed, such polyepoxides may be a linear or branched, homopolymer or copolymer (e.g., random, graft, block, etc.) containing terminal epoxy groups, skeletal oxirane units, and/ or pendent epoxy groups. The monomers employed to form such polyepoxides may vary. In one particular embodiment, for example, the polyepoxide modifier contains at least one epoxy-functional (meth)acrylic monomeric component. For example, suitable epoxy-functional (meth)acrylic monomers may include, but are not limited to, those containing 1,2-epoxy groups, such as glycidyl acrylate and glycidyl methacrylate. Other suitable epoxy-functional monomers include allyl glycidyl ether, glycidyl ethacrylate, and glycidyl itoconate. If desired, additional monomers may also be employed in the polyepoxide. Such monomers may vary and include, for example, ester monomers, (meth)acrylic monomers, olefin monomers, amide monomers, etc. In one particular embodiment, for example, the polyepoxide compound includes at least one linear or branched α-olefin monomer, such as those having from 2 to 20 carbon atoms and preferably from 2 to 8 carbon atoms. Specific examples include ethylene, propylene, 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are ethylene and propylene.

Another suitable monomer may include a (meth)acrylic monomer that is not epoxy-functional. Examples of such (meth)acrylic monomers may include methyl acrylate, ethyl acrylate, n-propyl acrylate, i-propyl acrylate, n-butyl acrylate, s-butyl acrylate, i-butyl acrylate, t-butyl acrylate, n-amyl acrylate, i-amyl acrylate, isobornyl acrylate, n-hexyl acrylate, 2-ethylbutyl acrylate, 2-ethylhexyl acrylate, n-octyl acrylate, n-decyl acrylate, methylcyclohexyl acrylate, cyclopentyl acrylate, cyclohexyl acrylate, methyl methacrylate, ethyl methacrylate, 2-hydroxyethyl methacrylate, n-propyl methacrylate, n-butyl methacrylate, i-propyl methacrylate, i-butyl methacrylate, n-amyl methacrylate, n-hexyl methacrylate, i-amyl methacrylate, s-butyl-methacrylate, t-butyl methacrylate, 2-ethylbutyl methacrylate, methylcyclohexyl methacrylate, cinnamyl methacrylate, crotyl methacrylate, cyclohexyl methacrylate, cyclopentyl methacrylate, 2-ethoxyethyl methacrylate, isobornyl methacrylate, etc., as well as combinations thereof. In one particular embodiment, the polyepoxide modifier is a terpolymer formed from an epoxy-functional (meth)acrylic monomeric component, α-olefin monomeric component, and non-epoxy functional (meth)acrylic monomeric component. For example, the polyepoxide modifier may be poly(ethylene-co-methylacrylate-co-glycidyl methacrylate). The epoxy functional monomer may be formed into a polymer using a variety of known techniques. For example, a monomer containing polar functional groups may be grafted onto a polymer backbone to form a graft copolymer. Such grafting techniques are well known in the art and described, for instance, in U.S. Pat. No. 5,179,164, which is incorporated herein in its entirety by reference thereto for all purposes. In other embodiments, a monomer containing epoxy functional groups may be copolymerized with a monomer to form a block or random copolymer using known free radical polymerization techniques, such as high pressure reactions, Ziegler-Natta catalyst reaction systems, single site catalyst (e.g., metallocene) reaction systems, etc.

While it is desirable to induce a reaction with the protein at a rate that is sufficient for the melt blending process, too much of a reaction can lead to degradation of the protein molecule, thereby making it difficult to draw into a material with the desired strength and elongation properties. In this regard, the present inventors have discovered that electrophilic reagents having a relatively low functionality are particularly effective in limiting the formation of disulfide crosslinks while still avoiding degradation of the protein. That is, the number of functional groups (e.g., epoxide or alkene) per molecule is typically less than 10, in some embodiments from 1 to 5, and in some embodiments, from 1 to 3. Further, the molecular weight of the electrophilic reagent is also typically small so that the compound itself does not alter the melt processablity of the protein. For example, the electrophilic reagent may have an average molecular weight of less than about 10,000 grams per mole, in some embodiments from about 20 to about 1,000 grams per mole, and in some embodiments, from about 50 to about 200 grams per mole. The amount of electrophilic reagent employed is also low enough to minimize protein degradation, but high enough to achieve the desired inhibition of crosslinking. Typically, the electrophilic reagent is present in an amount of from about 0.1 wt. % to about 20 wt. %, in some embodiments from about 1 wt. % to about 15 wt. %, and in some embodiments, from about 2 wt. % to about 12 wt. %, based on the weight of the protein employed in the composition. Depending on what other components are employed, the concentration of the electrophilic reagent in the entire composition may be the same or less than the ranges noted above. In certain embodiments, for example, the electrophilic reagent constitutes from about 0.01 wt. % to about 15 wt. %, in some embodiments from about 0.1 wt. % to about 12 wt. %, and in some embodiments, from about 0.5 wt. % to about 10 wt. %, based on the total weight of the composition.

Notwithstanding the above, catalysts may be employed in some embodiments to further increase the rate of the nucleophilic reaction. Such catalysts are well known to those skilled in the art. For instance, a base may be employed as a catalyst, such as trimethylamine, triethylamine, tributylamine, N-methylmorpholine, diethylamine, etc. Another suitable catalyst may be a phosphine compound, such as triphenylphosphine, tri-o-tolylphosphine, tri-m-tolylphosphine, tri-p-tolylphosphine, dimethylphenylphosphine, diethylphenylphosphine, ethyldiphenylphosphine, methyldiphenylphosphine, tributylphosphine, triethylphosphine, tricyclohexylphosphine, 1,2-bis(diphenylphosphino)ethane, 1,3-bis(diphenylphosphino)propane, and 1,4-bis(diphenylphosphino)butane.

C. Plasticizer

A plasticizer may also be employed in the composition to help render the protein more flowable and to help mediate the delivery of the electrophilic reagent into the internal protein structure. Suitable plasticizers may include, for instance, polyhydric alcohols, such as sugars (e.g., glucose, sucrose, fructose, raffinose, maltodextrose, galactose, xylose, maltose, lactose, mannose, and erythrose), sugar alcohols (e.g., erythritol, xylitol, malitol, mannitol, and sorbitol), polyols (e.g., ethylene glycol, glycerol, propylene glycol, dipropylene glycol, butylene glycol, and hexane triol), etc. Also suitable are hydrogen bond forming organic compounds that do not have a hydroxyl group, including urea and urea derivatives; anhydrides of sugar alcohols such as sorbitan; animal proteins such as gelatin; vegetable proteins such as sunflower protein, soybean proteins, cotton seed proteins; and mixtures thereof. Other suitable plasticizers may include phthalate esters, dimethyl and diethylsuccinate and related esters, glycerol triacetate, glycerol mono and diacetates, glycerol mono, di, and tripropionates, butanoates, stearates, lactic acid esters, citric acid esters, adipic acid esters, stearic acid esters, oleic acid esters, and other acid esters. Aliphatic carboxylic acids may also be used, such as lactic acid, maleic acid, acrylic acid, copolymers of ethylene and acrylic acid, polyethylene grafted with maleic acid, polybutadiene-co-acrylic acid, polybutadiene-co-maleic acid, polypropylene-co-acrylic acid, polypropylene-co-maleic acid, and other hydrocarbon based acids. A low molecular weight plasticizer is preferred, such as less than about 20,000 g/mol, preferably less than about 5,000 g/mol and more preferably less than about 1,000 g/mol.

If desired, the plasticizer may be selected to have a certain pH (refers to the pH prior to incorporation into the composition). For example, plasticizers having a relatively low pH can reduce the tendency of gluten proteins to aggregate during melt processing. Thus, when gluten proteins are employed, a plasticizer may be selected that has a pH of about 6 or less, in some embodiments from about 1 to about 5, and in some embodiments, from about 2 to about 4. Examples of such plasticizers may include aliphatic carboxylic acids, such as lactic acid, maleic acid, acrylic acid, etc. In other embodiments, it may be desirable to use plasticizers having a higher pH, such as when the plant protein is not generally sensitive to pH. For example, soy proteins generally lack the cysteine residues that lead to aggregation in gluten proteins. Thus, when employed, the soy protein may be used with plasticizers having a relatively wide range of pH levels. One example of such a plasticizer is glycerol, which has a pH of about 6.

The plasticizer is typically employed in an amount of from about 20 wt. % to about 80 wt. %, in some embodiments from about 30 wt. % to about 70 wt. %, and in some embodiments, from about 40 wt. % to about 60 wt. %, based on the weight of the protein employed in the composition. Likewise, the plasticizer may also constitute from about 1 wt. % to about 50 wt. %, in some embodiments from about 5 wt. % to about 40 wt. %, and in some embodiments, from about 10 wt. % to about 30 wt. %, based on the total weight of the entire composition.

D. Other Components

In addition to those noted above, still other additives may also be incorporated into the composition. For example, antioxidants may also be employed in the composition to neutralize radicals and prevent burning. Among other things, this may allow for elevated secondary processing temperatures while also preventing undesirable transformations in the protein structure due to radical formation during primary and secondary processing. Suitable antioxidants may include, for instance, acetylcysteine, 3-tert-butyl-4-hydroxyanisole, 2,6-di-tert-butyl-p-cresol, tert-butylhydroquinone, caffeic acid, chlorogenic acid, cysteine, cysteine hydrochloride, decylmercaptomethyl-imidazole, diamylhydroquinone, di-tert-butylhydroquinone, dicetyl thiodipropionate, digalloyl trioleate, dilauryl thiodipropionate, dimyristyl thiodipropionate, dioleyl tocopheryl methylsilanol, disodium rutinyl disulphate, distearyl thiodipropionate, ditridecyl thiodipropionate, dodecyl gallate, erythorbic acid, ethyl ferulate, ferulic acid, hydroquinone, p-hydroxyanisole, hydroxylamine hydrochloride, hydroxylamine sulphate, isooctyl thioglycolate, kojic acid, madecassicoside, methoxy-PEG-7-rutinyl succinate, nordihydroguaiaretic acid, octyl gallate, phenylthioglycolic acid, phloroglucinol, propyl gallate, rosmarinic acid, rutin, sodium erythorbate, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocophersolan, tocopherol (e.g., vitamin E) and its derivatives (e.g., vitamin E derivatives such as vitamin E acetate, vitamin E linoleate, vitamin E nicotinate and vitamin E succinate), o-tolylbiguanide, tris(nonylphenyl)phosphite, dexpanthenol, alpha-hydroxycarboxylic acids (e.g., glycolic acid, lactic acid, mandelic acid) and salts thereof, p-hydroxybenzoic esters (e.g., methyl, ethyl, propyl or butyl esters thereof), dimethyloldimethylhydantoin, N-acylamino acids and salts thereof (e.g., N-octanoylglycine, Lipacide C8G) and hinokitol. Of these, tocopherols and their derivatives are particularly desirable.

When employed, antioxidants may constitute amount of from about 0.01 wt. % to about 15 wt. %, in some embodiments from about 0.1 wt. % to about 10 wt. %, and in some embodiments, from about 0.5 wt. % to about 5 wt. %, based on the weight of the protein employed in the composition. Likewise, the antioxidants may also constitute from about 0.001 wt. % to about 10 wt. %, in some embodiments from about 0.05 wt. % to about 5 wt. %, and in some embodiments, from about 0.1 wt. % to about 2 wt. %, based on the total weight of the entire composition.

Further, a reducing agent may be employed in the composition to delay formation of disulfide bonds from sulfhydryl groups (thiol) by donating protons to the thiol group, thereby keeping them in their reduced state. Among other things, the delay of the formation of disulfide bonds can help provide greater time for the electrophilic reagent to react with the sulfhydryl groups. Particularly suitable reducing agents include, for instance, alkali metal or ammonium sulfites, bisulfites, metabisulfites, or nitrites (e.g., sodium metabisulfite), carboxylic acids, cysteine, cysteamine, mercaptoethanol, etc., as well as mixtures thereof. Organic carboxylic acids are particularly suitable, such as acrylic acid, methacrylic acid, malonic acid, succinic acid, salicylic acid, sulfosalicylic acid, adipic acid, maleic acid, malic acid, oleic acid, gallic acid, tartaric acid, citric acid, formic acid, acetic acid, glycolic acid, oxalic acid, tartaric acid (e.g., dextotartaric acid, mesotartaric acid, etc.), propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic acid, etc.; phenols, such as pyrogallol(benzene-1,2,3-triol), pyrocatechol(benezenediol), etc.; blends thereof, and so forth. Anhydrides (e.g., maleic anhydride) and salts of organic acids may also be employed. Particularly suitable organic acids for use in the present invention are those having an acid dissociation constant ($pK_a$) ranging from 0 to about 8, in some embodiments from about 1 to about 5, and in some embodiments, from about 2 to about 5, determined at 25° C., such as lactic acid ($pK_a$ of 3.85), salicylic acid ($pK_a$ of 2.97), and acetic acid ($pK_a$ of 4.76).

When employed, reducing agents may constitute amount of from about 0.01 wt. % to about 15 wt. %, in some embodiments from about 0.1 wt. % to about 10 wt. %, and in some embodiments, from about 0.5 wt. % to about 5 wt. %, based on the weight of the protein employed in the composition. Likewise, the reducing agents may also constitute from about 0.001 wt. % to about 10 wt. %, in some embodiments from about 0.05 wt. % to about 5 wt. %, and in some embodiments, from about 0.1 wt. % to about 2 wt. %, based on the total weight of the entire composition.

Starch polymers, which are often found in commercially available protein compositions, may also be employed in the present invention. When employed, such starch polymers typically constitute 5 wt. % to about 60 wt. %, in some embodiments from about 10 wt. % to about 50 wt. %, and in some embodiments, from about 20 wt. % to about 40 wt. %, based on the weight of protein. The starch polymers may likewise constitute from about 1 wt. to about 50 wt. % of the composition, in some embodiments from about 5 wt. % to about 40 wt. %, and in some embodiments, from about 10 wt. % to about 30 wt. % of the entire composition.

Although starch polymers are produced in many plants, typical sources includes seeds of cereal grains, such as corn, waxy corn, wheat, sorghum, rice, and waxy rice; tubers, such as potatoes; roots, such as tapioca (i.e., cassava and manioc), sweet potato, and arrowroot; and the pith of the sago palm. Chemically modified starches may also be employed as they typically possess a higher degree of water sensitivity, and therefore can help facilitate water sensitivity during use. Such chemically modified starches may be obtained through typical processes known in the art (e.g., esterification, etherification, oxidation, acid hydrolysis, enzymatic hydrolysis, etc.). Starch ethers and/or esters may be particularly desirable, such as hydroxyalkyl starches, carboxymethyl starches, etc. The hydroxyalkyl group of hydroxylalkyl starches may contain, for instance, 2 to 10 carbon atoms, in some embodiments from 2 to 6 carbon atoms, and in some embodiments, from 2 to 4 carbon atoms. Representative hydroxyalkyl starches such as hydroxyethyl starch, hydroxypropyl starch, hydroxybutyl starch, and derivatives thereof. Starch esters, for instance, may be prepared using a wide variety of anhydrides (e.g., acetic, propionic, butyric, and so forth), organic acids, acid chlorides, or other esterification reagents. The degree of esterification may vary as desired, such as from 1 to 3 ester groups per glucosidic unit of the starch. The starch polymer may contain different weight percentages of amylose and amylopectin, different polymer molecular weights, etc. High amylose starches contain greater than about 50% by weight amylose and low amylose starches contain less than about 50% by weight amylose. Although not required, low amylose starches having an amylose content of from about 10% to about 40% by weight, and in some embodiments, from about 15% to about 35% by weight, are particularly suitable for use in the present invention. Examples of such low amylose starches include corn starch and potato starch, both of which have an amylose content of approximately 20% by weight, Dispersion aids may also be employed to help create a uniform dispersion of the oil/protein/plasticizer and retard or prevent separation of the composition into constituent phases. When employed, the dispersion aid(s) typically constitute from about 0.001 wt. % to about 10 wt. %, in some embodiments from about 0.01 wt. % to about 5 wt. %, and in some embodiments, from about 0.1 wt. % to about 4 wt. %, based on the weight of the protein in the composition. Although any dispersion aid may generally be employed in the present invention, surfactants having a certain hydrophilic/lipophilic balance may improve the long-term stability of the composition. As is known in the art, the relative hydrophilicity or lipophilicity of an emulsifier can be characterized by the hydrophilic/lipophilic balance ("HLB") scale, which measures the balance between the hydrophilic and lipophilic solution tendencies of a compound. The HLB scale ranges from 0.5 to approximately 20, with the lower numbers representing highly lipophilic tendencies and the higher numbers representing highly hydrophilic tendencies. In some embodiments of the present invention, the HLB value of the surfactants is from about 1 to about 15, in some embodiments from about 1 to about 12 and in some embodiments, from about 2 to about 10. If desired, two or more surfactants may be employed that have HLB values either below or above the desired value, but together have an average HLB value within the desired range.

One particularly suitable class of surfactants for use in the present invention are nonionic surfactants, which typically have a hydrophobic base (e.g., long chain alkyl group or an alkylated aryl group) and a hydrophilic chain (e.g., chain containing ethoxy and/or propoxy moieties). For instance, some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglyceride or diglycerides of long chain alcohols, and mixtures thereof. In one particular embodiment, the nonionic surfactant may be a fatty acid ester, such as a sucrose fatty acid ester, glycerol fatty acid ester, propylene glycol fatty acid ester, sorbitan fatty acid ester, pentaerythritol fatty acid ester, sorbitol fatty acid ester, and so forth. The fatty acid used to form such esters may be saturated or unsaturated, substituted or unsubstituted, and may contain from 6 to 22 carbon atoms, in some embodiments from 8 to 18 carbon atoms, and in some embodiments, from 12 to 14 carbon atoms. In one particular embodiment, mono- and di-glycerides of fatty acids may be employed in the present invention.

To better enhance the benefits to consumers, other optional ingredients may also be used. For instance, some classes of ingredients that may be used include, but are not limited to antimicrobial actives; anti-reddening agents, such as aloe extract; astringents-cosmetic (induce a tightening or tingling sensation on skin); colorants (impart color to the product); deodorants (reduce or eliminate unpleasant odor and protect against the formation of malodor on body surfaces); emulsifiers; fragrances (consumer appeal); opacifiers (reduce the clarity or transparent appearance of the product); preservatives; skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); and thickeners (to increase viscosity).

While a wide variety of different components may be employed, it is typically desired that the composition is formed without the use of solvents, particularly organic solvents, such as organic alcohols (e.g., ethanol). Not only does this enhance manufacturing efficiency, but it also limits the evaporation of certain additives that might otherwise be encountered during removal of the solvent. While the composition may be generally free of such solvents, it should of course be understood that a small amount may still be present in the resulting composition. Regardless, the composition typically contains solvents in an amount less than about 20 wt. %, in some embodiments less than about 10 wt. %, and in some embodiments, from about 0.01 wt. % to about 5 wt. %.

II. Melt Processing Technique

As indicated above, the composition of the present invention is formed by processing the components together in a melt blending device (e.g., extruder). The mechanical shear and heat provided by the device allows the components to be blended together in a highly efficient manner without the use of a solvent. Batch and/or continuous melt blending techniques may be employed in the present invention. For example, a mixer/kneader, Banbury mixer, Farrel continuous mixer, single-screw extruder, twin-screw extruder, roll mill, etc., may be utilized. One particularly suitable melt-blending device is a co-rotating, twin-screw extruder (e.g., USALAB twin-screw extruder available from Thermo Electron Corporation of Stone, England or an extruder available from Werner-Pfreiderer from Ramsey, N.J.). The raw materials (e.g., protein, plasticizer, electrophilic reagent, etc.) may be supplied to the melt blending device separately and/or as a blend. For example, the protein and other optional additives (e.g., reducing agent, antioxidants, etc.) may be initially fed to a feeding port of the twin-screw extruder. Thereafter, the plasticizer and electrophilic reagent may be injected into the extruder downstream from the protein. Alternatively, the components may be simultaneously fed to the feed throat of the extruder or separately at a different point along its length.

Regardless, the materials are dispersively blended under low shear/pressure and at a low temperature to minimize protein dissociation associated with aggregation. Nevertheless, the temperature is still typically at or above the softening point of the protein. For example, melt blending typically occurs at a temperature of from about 20° C. to about 100° C., in some embodiments, from about 30° C. to about 80° C., and in some embodiments, from about 40° C. to about 70° C. Likewise, the apparent shear rate during melt blending may range from about 100 seconds$^{-1}$ to about 5,000 seconds$^{-1}$, in some embodiments from about 200 seconds$^{-1}$ to about 2,000 seconds$^{-1}$, and in some embodiments, from about 400 seconds$^{-1}$ to about 1,200 seconds$^{-1}$. The apparent shear rate is equal to $4Q/\pi R^3$, where Q is the volumetric flow rate ("m$^3$/s") of the polymer melt and R is the radius ("m") of the capillary (e.g., extruder die) through which the melted polymer flows. The apparent melt viscosity of the resulting composition may be relatively low, such as from about 1 to about 100 Pascal seconds (Pa·s), in some embodiments from about 5 to about 60 Pa·s, and in some embodiments, from about 20 to about 50 Pa·s, as determined at a temperature of 160° C. and a shear rate of 1000 sec$^{-1}$. The melt flow index (190° C., 2.16 kg) of the composition may also range from about 0.05 to about 50 grams per 10 minutes, in some embodiments from about 0.1 to about 15 grams per 10 minutes, and in some embodiments, from about 0.5 to about 5 grams per 10 minutes.

Once formed, the composition of the present invention may be used in a variety of forms, such as particles, lotion, cream, jelly, liniment, ointment, salve, oil, foam, gel, film, fibers, wash, coating, liquid, capsule, tablet, concentrate, etc. In one particular embodiment, for example, the composition may be formed into a film, either alone or in conjunction with an additional film-forming material. The film may be used in a wide variety of applications, such as in the packaging of items (e.g., food products, medical products, garments, garbage, absorbent articles (e.g., diapers), etc. The film may have a mono-layered or multi-layered structure. Multilayer films normally contain at least one base layer and at least one skin layer, but may contain any number of layers desired. The base layer and/or the skin layer may contain the composition of the present invention. Any known technique may be used to form a film from the compounded material, including blowing, casting, flat die extruding, etc. In one particular embodiment, the film may be formed by a blown process in which a gas (e.g., air) is used to expand a bubble of the extruded polymer blend through an annular die. The bubble is then collapsed and collected in flat film form. Processes for producing blown films are described, for instance, in U.S. Pat. No. 3,354,506 to Raley; U.S. Pat. No. 3,650,649 to Schippers; and U.S. Pat. No. 3,801,429 to Schrenk et al., as well as U.S. Patent Application Publication Nos. 2005/0245162 to McCormack, et al. and 2003/0068951 to Boggs, et al., all of which are incorporated herein in their entirety by reference thereto for all purposes. In yet another embodiment, however, the film is formed using a casting technique.

Besides being formed into a film, the composition of the present invention may also be formed into particles and applied to other types of articles. Powderization may be accomplished using any of a variety of known techniques. Suitable pulverizing techniques may include, for instance, cryogenic disk mill or hammer mill, solid state shear pulverization using cold extrusion technology, double stream mills (e.g., Type PSKM or PPSM mills available from Pallmann Industries), and other known powderization methods. Cryogenic downsizing techniques or cold extrusion pulverization techniques may be particularly suitable as such techniques limit the degree to which the volatile botanical oil is heated and lost during powder formation. Examples of such techniques are described in more detail, for instance, in U.S. Pat. No. 5,395,055 to Shutov, et al., which is incorporated herein in its entirety by reference thereto for all purposes. The shape of the particles may vary as desired, such as spherical, nodular, flake, etc. The average size of the particles may vary, such as from about 10 to about 3,000 micrometers, in some embodiments from about 50 to about 800 micrometers, and in some embodiments, from about 100 to about 600 micrometers, can help achieve a good balance between stability and releasibility. The composition of the present invention may also be employed in injection molded articles. For instance, the article may be a container, dispenser, tab, surgical instrument (e.g., scalpels, scissors, retractors, suction tubes, probes, etc.); implant (e.g., bone plates, prosthetics, plates, screws, etc.); and so forth. In one particular embodiment, the molding material is used to form a wet wipe container. The configuration of the container may vary as is known in the art, such as described in U.S. Pat. No. 5,687,875 to Watts, et al.; U.S. Pat. No. 6,568,625 to Faulks, et al.; U.S. Pat. No. 6,158,614 to Haines, et al.; U.S. Pat. No. 3,973,695 to Ames; U.S. Pat. No. 6,523,690 to Buck, et al.; and U.S. Pat. No. 6,766,919 to Huang, et al., which are incorporated herein in their entirety by reference thereto for all purposes.

Regardless of its form, the composition of the present invention may be employed in a wide variety of different application for a variety of purposes. In one particular embodiment, for example, the protein composition may be employed in combination with a botanical oil to form a stable antimicrobial composition. Namely, it is believed that the physical structure of the protein can effectively encapsulate the botanical oil and inhibit its premature release. This can help enhance the long term stability of the oil and, in turn, antimicrobial efficacy.

Botanical oils employed in the composition as antimicrobial actives may be an "essential" oils extracted from a plant, as well as isolated or purified from an essential oil, or made synthetically to mimic a compound derived from a plant (e.g., synthetically made thymol). The botanical oils are generally soluble in lipids and believed to exhibit antimicrobial efficacy due to their ability to cause damage to the lipid component of the cell membrane in microorganisms, thereby inhibiting their proliferation. Essential oils are derived from herbs, flowers, trees, and other plants, and are typically present as tiny droplets between the cells of the plants and may be extracted by methods known to those of skill in the art (e.g., steam distillation, enfleurage (i.e., extraction using fat(s)), maceration, solvent extraction, or mechanical pressing). Examples of suitable essential oils for use in the present invention may include, for instance, anise oil, lemon oil, orange oil, oregano, rosemary oil, wintergreen oil, thyme oil, lavender oil, clove oil, hops, tea tree oil, citronella oil, wheat oil, barley oil, lemongrass oil, cedar leaf oil, cedar wood oil, cinnamon oil, fleagrass oil, geranium oil, sandalwood oil, violet oil, cranberry oil, eucalyptus oil, vervain oil, peppermint oil, gum benzoin, basil oil, fennel oil, fir oil, balsam oil, menthol, ocmea origanum oil, *Hydastis carradensis* oil, *Berberidaceae daceae* oil, Ratanhiae and *Curcuma longa* oil, sesame oil, macadamia nut oil, evening primrose oil, Spanish sage oil, Spanish rosemary oil, coriander oil, thyme oil, pimento berries oil, rose oil, bergamot oil, rosewood oil, chamomile oil, sage oil, clary sage oil, cypress oil, sea fennel oil, frankincense oil, ginger oil, grapefruit oil, jasmine oil, juniper oil, lime oil, mandarin oil, marjoram oil, myrrh oil, neroli oil, patchouli oil, pepper oil, black pepper oil, petitgrain oil, pine oil, rose otto oil, spearmint oil, spikenard oil, vetiver oil, or ylang ylang. Still other essential oils known to those of skill in the art are also contemplated as being useful within the context of the present invention (e.g., International Cosmetic Ingredient Dictionary, 10$^{th}$ and 12$^{th}$ editions, 2004 and 2008, respectively, which are incorporated by reference).

In one embodiment, carvacrol and thymol-containing oils are purified from the species *Origanum vulgare* of a hirtum variety. Ideally this is a hybrid strain that produces high quality oils, but is not limited to this genus, species or strain. The oil extract may also be obtained from a plant of the genus *Nepeta* including, but not limited to species *Nepeta racemosa* (catmint), *Nepeta citriodora, Nepeta Nepeta hindostoma, Nepeta lanceolata, Nepeta leucophylla, Nepeta longiobracteata, Nepeta mussinii, Nepeta nepetella, Nepeta sibthorpii, Nepeta subsessilis, Nepeta tuberosa, Thymus glandulosus, Thymus hyemalis, Thymus vulgaris* and *Thymus zygis*.

As indicated above, isolates and/or derivatives of essential oils may also be employed in the present invention. For example, monoterpene phenols are particularly suitable for use in the present invention, which may be isolated and purified from plant oil extracts, or made synthetically by known methods. Suitable monoterpene phenols may include, for instance, thymol, carvacrol, eucalyptol, etc. Thymol(isopropyl-cresol) is one particularly suitable monoterpene phenol, which is a crystalline substance that has a boiling point of about 238° C. at atmospheric pressure. Carvacrol(isopropyl-o-cresol), an isomer of thymol, is another suitable compound. Carvacrol is a liquid with a boiling point of about 233° C. at atmospheric pressure. Thymol and carvacrol, as well as isomers thereof, may be derived from plant oil extracts or synthesized. For example, carvacrol may be synthesized by the reaction of nitrous acid with 1-methyl-2-amino-4-propyl benzene. In addition to being employed in an isolated or pre-synthesized form, essential oils containing the monoterpene phenols as major constituents may be employed, with the final concentrations of the monoterpene phenols being within the ranges provided herein. The term "major constituent" generally refers to those essential oils having monoterpene phenols in an amount of more than 50 wt. %. It is well-known in the art that such essential oils may also contain lesser amounts of other constituents, such as non-aromatic terpene compounds. Essential oils with organic phenolic compounds as the major constituent include, for example, anise oil, bay oil terpineless, clove bud, clove leaf, clove oil, clove stem, origanum oil, Peru balsam, pimento oil, eucalyptus oil, and thyme oil.

Due to the stability achieved by the antimicrobial composition of the present invention, a relatively small amount of botanical oils may be employed and still achieve the desired antimicrobial efficacy. More particularly, the composition may employ botanical oils in an amount of from about 0.1 wt. % to about 30 wt. %, in some embodiments from about 0.5 wt. % to about 20 wt. %, and in some embodiments, from about 1 wt. % to about 10 wt. %.

If desired, the protein/botanical oil composition may be applied to a wipe to enhance the degree of surface contact with microorganisms. Such wipes may be used to reduce microbial or viral populations on a hard surface (e.g., sink, table, counter, sign, and so forth) or surface on a user/patient (e.g., skin, mucosal membrane, such as in the mouth, nasal passage, stomach, vagina, etc., wound site, surgical site, and so forth). The wipe may provide an increased surface area to facilitate contact of the composition with microorganisms. In addition, the wipe may also serve other purposes, such as providing water absorption, barrier properties, etc. The wipe may also eliminate microorganisms through frictional forces imparted to the surface.

The wipe may be formed from any of a variety of materials as is well known in the art. Typically, however, the wipe includes a fibrous web that contains absorbent fibers. For example, the wipe may be a paper product containing one or more paper webs, such as facial tissue, bath tissue, paper towels, napkins, and so forth. The paper product may be single-ply in which the web forming the product includes a single layer or is stratified (i.e., has multiple layers), or multi-ply, in which the webs forming the product may themselves be either single or multi-layered. Normally, the basis weight of such a paper product is less than about 120 grams per square meter ("gsm"), in some embodiments less than about 80 gsm, in some embodiments less than about 60 grams per square meter, and in some embodiments, from about 10 to about 60 gsm. Any of a variety of materials can also be used to form the paper web(s) of the product. For example, the material used to make the paper product may include absorbent fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable for the present invention include those available from Kimberly-Clark Corporation under the trade designations "Longlac-19". Hardwood fibers, such as eucalyptus, maple, birch, aspen, and so forth, can also be used. In certain instances, eucalyptus fibers may be particularly desired to increase the softness of the web. Eucalyptus fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other natural fibers can also be used in the present invention, such as abaca, sabai grass, milkweed floss, pineapple leaf, bamboo, algae, and so forth. In addition, in some instances, synthetic fibers can also be utilized.

If desired, the absorbent fibers (e.g., pulp fibers) may be integrated with synthetic fibers to form a composite. Synthetic thermoplastic fibers may also be employed in the nonwoven web, such as those formed from polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; polyhydroxyalkanoate; copolymers thereof; and so forth. Because many synthetic thermoplastic fibers are inherently hydrophobic (i.e., non-wettable), such fibers may optionally be rendered more hydrophilic (i.e., wettable) by treatment with a surfactant solution before, during, and/or after web formation. Other known methods for increasing wettability may also be employed, such as described in U.S. Pat. No. 5,057,361 to Savovitz, et al., which is incorporated herein in its entirety by reference thereto for all purposes. The relative percentages of such fibers may vary over a wide range depending on the desired characteristics of the composite. For example, the composite may contain from about 1 wt. % to about 60 wt. %, in some embodiments from 5 wt. % to about 50 wt. %, and in some embodiments, from about 10 wt. % to about 40 wt. % synthetic polymeric fibers. The composite may likewise contain from about 40 wt. % to about 99 wt. %, in some embodiments from 50 wt. % to about 95 wt. %, and in some embodiments, from about 60 wt. % to about 90 wt. % absorbent fibers.

Composites, such as described above, may be formed using a variety of known techniques. For example, a nonwoven composite may be formed that is a "coform material" that contains a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes. Alternatively, the nonwoven composite may be formed be formed by hydraulically entangling staple length fibers and/or filaments with high-pressure jet streams of water. Various techniques for hydraulically entangling fibers are generally are disclosed, for example, in U.S. Pat. No. 3,494,821 to Evans and U.S. Pat. No. 4,144,370 to Bouolton, which are incorporated herein in their entirety by reference thereto for all purposes. Hydraulically entangled nonwoven composites of continuous filaments (e.g., spunbond web) and natural fibers (e.g., pulp) are disclosed, for example, in U.S. Pat. No. 5,284,703 to Everhart, et al. and U.S. Pat. No. 6,315,864 to Anderson, et al., which are incorporated herein in their entirety by reference thereto for all purposes. Hydraulically entangled nonwoven composite of staple fiber blends (e.g., polyester and rayon) and natural fibers (e.g., pulp), also known as "spunlaced" fabrics, are described, for example, in U.S. Pat. No. 5,240,764 to Haid, et al., which is incorporated herein in its entirety by reference thereto for all purposes.

Regardless of the materials or processes utilized to form the wipe, the basis weight of the wipe is typically from about 20 to about 200 grams per square meter ("gsm"), and in some embodiments, between about 35 to about 100 gsm. Lower basis weight products may be particularly well suited for use as light duty wipes, while higher basis weight products may be better adapted for use as industrial wipes.

The wipe may assume a variety of shapes, including but not limited to, generally circular, oval, square, rectangular, or irregularly shaped. Each individual wipe may be arranged in a folded configuration and stacked one on top of the other to provide a stack of wet wipes. Such folded configurations are well known to those skilled in the art and include c-folded, z-folded, quarter-folded configurations and so forth. For example, the wipe may have an unfolded length of from about 2.0 to about 80.0 centimeters, and in some embodiments, from about 10.0 to about 25.0 centimeters. The wipes may likewise have an unfolded width of from about 2.0 to about 80.0 centimeters, and in some embodiments, from about 10.0 to about 25.0 centimeters. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing. Various suitable dispensers, containers, and systems for delivering wipes are described in U.S. Pat. No. 5,785,179 to Buczwinski, et al.; U.S. Pat. No. 5,964,351 to Zander; U.S. Pat. No. 6,030,331 to Zander; U.S. Pat. No. 6,158,614 to Haynes, et al.; U.S. Pat. No. 6,269,969 to Huang, et al.; U.S. Pat. No. 6,269,970 to Huang, et al.; and U.S. Pat. No. 6,273,359 to Newman, et al., which are incorporated herein in their entirety by reference thereto for all purposes.

The composition may be incorporated into the wipe in a variety of different ways. For example, the composition may be applied to a surface of the wipe using known techniques, such as printing, dipping, spraying, melt extruding, coating (e.g., solvent coating, powder coating, brush coating, etc.), foaming, and so forth. If desired, the composition may be applied in a pattern that covers from about 5% to about 95%, in some embodiments from about 10% to about 90%, and in some embodiments, from about 20% to about 75% of a surface of the wipe. Such patterned application may have various benefits, including enhanced aesthetic appeal, improved absorbency, etc. The particular type or style of the pattern is not a limiting factor of the invention, and may include, for example, any arrangement of stripes, bands, dots, or other geometric shape. The pattern may include indicia (e.g., trademarks, text, and logos), floral designs, abstract designs, any configuration of artwork, etc. It should be appreciated that the "pattern" may take on virtually any desired appearance. The composition may also be blended with the fibers used to form the wipe. This may be particularly useful when the composition is in the form of particles. For example, such particles may be blended with the absorbent fibers (e.g., pulp fibers, staple fibers, etc.) during hydraulic entanglement, coforming, etc. The particles may also be incorporated into the thermoplastic material of the wipe (e.g., meltblown web) using known techniques.

The amount of the composition on the wipe may vary depending on the nature of the substrate and its intended application. For example, the add-on level of the composition may be from about 5% to about 100%, in some embodiments from about 10% to about 80%, and in some embodiments, from about 20% to about 70%. The "add-on level" is determined by subtracting the weight of the untreated substrate from the weight of the treated substrate, dividing this calculated weight by the weight of the untreated substrate, and then multiplying by 100%. Lower add-on levels may provide optimum functionality of the substrate, while higher add-on levels may provide optimum antimicrobial efficacy.

To use the composition, an aqueous solution may simply be added, thereby dispersing the protein and releasing the botanical oil. The aqueous solution may contain only water, or it may contain water in combination with other components. For example, a weak acid may be employed to help disperse the protein and facilitate the release of the oil upon contact with the aqueous solution. Suitable acids for this purpose may include, for instance, organic carboxylic acids, such as citric acid, oxalic acid, lactic acid, acetic acid, etc. Regardless, the present inventors have surprisingly discovered that the amount of the botanical oil released into the aqueous solution can be even greater than the normal solubility limit of the oil in water. Without intending to be limited by theory, it is believed that this can be achieved because the physical structure of the protein is able to effectively "carry" the volatile into the released solution. For example, the solubility limit of thymol in water (at 25° C.) is typically about 0.1 wt. %. When released from the composition of the present invention, however, the concentration of thymol in the released solution can be greater than 0.1 wt. %, in some embodiments greater than about 0.5 wt. %, in some embodiments from about 1 wt. % to about 10 wt. %., and in some embodiments, from about 2 wt. % to about 8 wt. %.

The present invention may be better understood with reference to the following examples.

Materials Employed

WhetPro® 75 vital wheat gluten (75% protein, 25% starch) was obtained from ADM.
Emery 917 Glycerine (or Glycerol) was obtained from Cognis Oleochemicals.
Excel P-40S (mono-diglyceride dispersion aid) was obtained from Kao Corp.
Glycidyl hexadecyl ether ("GHE") (molecular weight of 298.5 grams per mole) was obtained from Sigma-Aldrich Co.
Poly(ethylene glycol)ethyl ether methacrylate ("PEG-EEMA") (molecular weight of 246 grams per mole) was obtained from Sigma-Aldrich Co.
DECONOX™ MTS-90 (≥90% total tocopherols, ≤20% d-α tocopherol, oil) was obtained from ADM.
Salicylic acid was obtained from Sigma-Aldrich Co.

Test Methods

Tensile Properties:

The strip tensile strength values were determined in substantial accordance with ASTM Standard D-5034. A constant-rate-of-extension type of tensile tester was employed. The tensile testing system was a Sintech 1/D tensile tester, which is available from Sintech Corp. of Cary, N.C. The tensile tester was equipped with TESTWORKS 4.08B software from MTS Systems Corporation to support the testing. An appropriate load cell was selected so that the tested value fell within the range of 10-90% of the full scale load. The film samples were initially cut into dog-bone shapes with a center width of 3.0 mm before testing. The samples were held between grips having a front and back face measuring 25.4 millimeters×76 millimeters. The grip faces were rubberized, and the longer dimension of the grip was perpendicular to the direction of pull. The grip pressure was pneumatically maintained at a pressure of 40 pounds per square inch. The tensile test was run using a gauge length of 18.0 millimeters and a break sensitivity of 40%. Five samples were tested by applying the test load along the machine-direction and five samples were tested by applying the test load along the cross direction. During the test, samples were stretched at a crosshead speed of abut 127 millimeters per minute until breakage occurred. The modulus, peak stress, peak strain (i.e., % strain at peak load), and elongation were measured.

Viscosity:

To measure viscosity, the sample was placed on a cone and plate Brookfield CAP 2000+H Viscometer at a temperature of 50° C. Using spindle CAP #5, viscosity was measured as temperature was increased by approximately 10° C. every 3 minutes up to 140° C. Shear rate and spindle rpm was held constant at 83.1 sec$^{-1}$ and 25 rpm, respectively.

Example 1

Figure 1:
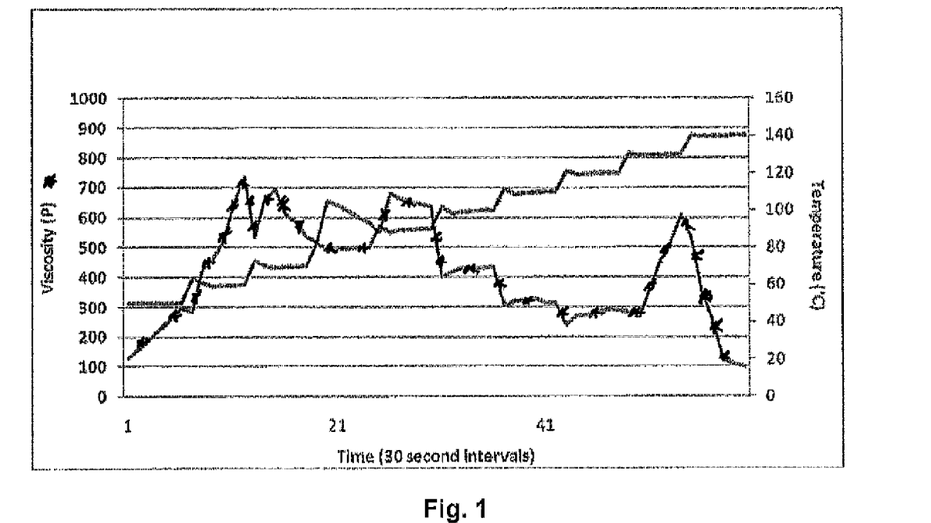
FIG. 1 is a graph showing the viscosity of a sample containing 40 wt. % gluten and 60 wt. % glycerol (Example 1) at various temperatures.

A mixture of 40 wt. % vital wheat protein and 60 wt. % glycerol was initially formed and tested for viscosity at various temperatures. More particularly, viscosity was taken on a cone and plate Brookfield CAP 2000+H Viscometer (25 rpms). Viscosity was measured as temperature step increases were implemented and shear rate was held constant. The results are shown in FIG. 1. As illustrated, the optimal temperatures occurred between 50° C. to 70° C., when the protein was taken in the plasticizer through interstices while maintaining a quaternary protein structure. When 90° C. was reached, viscosity began to behave classically in that as temperature increased, viscosity decreased. When the temperature reached 130° C., there was a large spike in viscosity followed by a drop off. It is believed that this is a result of protein aggregation (polypeptide network formation from disassociated polypeptides).

Example 2

Figure 2:
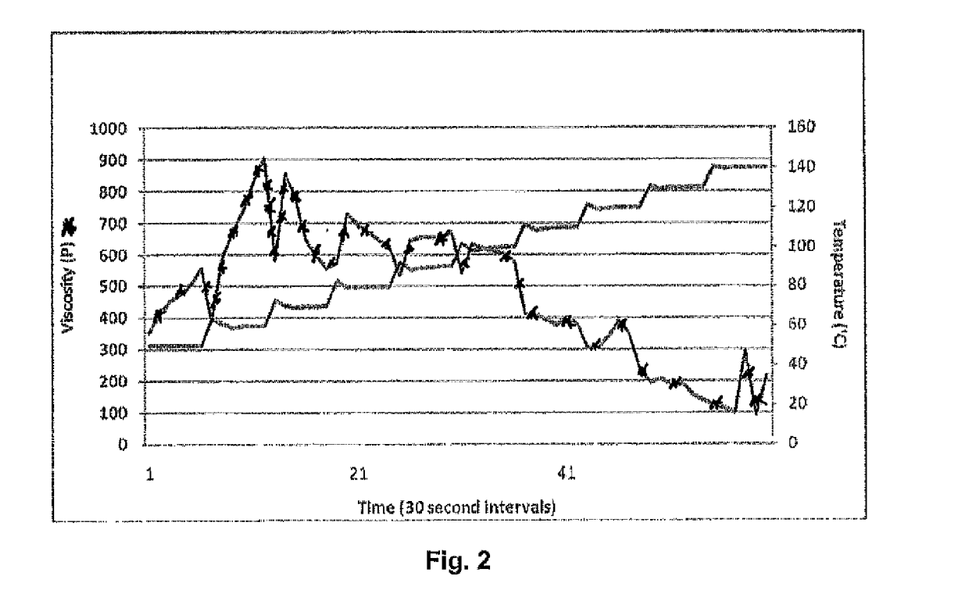
FIG. 2 is a graph showing the viscosity of a sample containing 36.9 wt. % vital wheat protein, 55.3 wt. % glycerol, and 7.8 wt. % glycidyl hexadecyl ether ("GHE") (Example 2) at various temperatures.

A mixture of 36.9 wt. % vital wheat protein, 55.3 wt. % glycerol, and 7.8 wt. % glycidyl hexadecyl ether ("GHE") was initially formed and tested for viscosity at various temperatures as described in Example 1. The resulting viscosity profile is shown in FIG. 2. As illustrated, the optimal swelling temperature was 50° C. to 70° C.; however, there was no aggregation peak at 130° C. It is believed that the absence of an aggregation peak indicated that the addition of GHE was absorbed by the vital wheat gluten during the 50° C.-70° C. temperatures. When dissociation of the polypeptide was initiated at elevated temperatures, the sulfhydryl groups reacted with GHE rather than creating crosslinks, thus preventing polypeptide network formation.

Example 3

A "PRISM USALAB 16" lab scale twin screw extruder was employed to melt process a sample of 70 wt. % protein (WhetPro® 75), 24 wt. % glycerol, 5 wt. % GHE, and 1 wt. % DECONOX™ MTS-90. The extruder contained eleven (11) different zones, although zones 1 through 5 were not utilized in this Example. Temperature zone 11 was a strand die. The temperature profile of zones 6 to 11 was 32° C., 38° C., 44° C., 55° C., 70° C., and 70° C., respectively. The protein was added to the extruder at zone 6 at a feed rate of 0.5 lbs/hr. A pre-blended mixture of 80 wt. % glycerol, 18 wt. % GHE, and 2 wt. % MTS-90 was then added at zone 7 at a feed rate of 0.21 lb/hr. The mixture was added on a hot plate to melt the GHE. The screw configuration was composed of conveying elements at zones 6 and 7, kneading blocks at zones 8 and 9, and conveying elements at zone 10. The screw speed was 50 rpm.

The material was successfully extruded, producing a smooth homogeneous, pelletizable strand. The process was consistent at keeping a low die pressure at about 17 bars and a low torque value of about 7 Nm.

Example 4

A "PRISM USALAB 16" lab scale twin screw extruder was employed to melt process a sample of 68.5 wt. % protein (WhetPro® 75), 23.2 wt. % glycerol, 5.6 wt. % GHE, 0.95 wt. % salicylic acid, 0.95 wt. % Excel P-40S, and 0.89 wt. % DECONOX™ MTS-90. The extruder contained eleven (11) different zones, although zones 1 through 5 were not utilized in this Example. Temperature zone 11 was a strand die. The temperature profile of zones 6 to 11 was 32° C., 37° C., 43° C., 53° C., 70° C., and 70° C., respectively. A dry blend of 97.3 wt. % protein, 1.35 wt. % salicylic acid, and 1.35 wt. % Excel P-40S was added to the extruder at zone 6 at a feed rate of 0.5 lbs/hr. A pre-blended mixture of 78.2 wt. % glycerol, 18.8 wt. % GHE, and 3.0 wt. % MTS-90 was then added at zone 7 at a feed rate of 0.21 lb/hr. The mixture was added on a hot plate to melt the GHE. The screw configuration was composed of conveying elements at zones 6 and 7, kneading blocks at zones 8 and 9, and conveying elements at zone 10. The screw speed was 50 rpm.

The material was successfully extruded, producing a smooth homogeneous, pelletizable strand. The process was consistent at keeping a low die pressure at about 21 bars and a low torque value of about 10 Nm.

Example 5

A material was formed as described in Example 4, except that poly(ethylene glycol) ethyl ether methacrylate ("PEG-EEMA") was employed rather than GHE.

The material was successfully extruded, producing a smooth homogeneous, pelletizable strand. The process was consistent at keeping a low die pressure at about 10 bars and a low torque value of about 5 Nm. The compositions of Examples 4 and 5 were also pressed into a film using a 2-3 inch strand pressed at 10,000 lbs for a dwell time of 1 minute at a temperature of 170° C. Mechanical properties of the films were then tested as described above. A control film containing 70 wt. % gluten and 30 wt. % glycerol was also tested. The results are set forth below in Table 1.

TABLE 1

Mechanical Properties of Examples 4-5

| Avg. Test Results | Control | Example 4 | Example 5 |
|---|---|---|---|
| Peak Stress (MPa) | 8.5 | 3.8 | 3.3 |
| Elongation (%) | 142 | 60 | 44 |
| Modulus (MPa) | 66 | 47 | 64 |
| Thickness (mil) | 6.8 | 5.5 | 7.3 |

Example 6

A "PRISM USALAB 16" lab scale twin screw extruder was employed to melt process a sample of Vital wheat gluten (Meelunie America Inc), glycerol, and Excel P-40S. The extruder contained eleven (11) different zones. All zones were set to a temperature of 60° C., A dry blend of 98 wt. % protein and 2 wt. % Excel P-40S was added to the extruder at zone 1 at a feed rate of 1.05 lbs/hr. Glycerol was then added at zone 2 at a feed rate of 0.45 lb/hr. The screw configuration was composed of conveying elements at zones 6 and 7, kneading blocks at zones 8 and 9, and conveying elements at zone 10. The screw speed was 40 rpm. It was determined that no material exited the extruder due to "over torque" of the motor.

This result was an attribute of a left hand screw preceding a kneading block section located at zone 6, creating back up of the material and high shear mixing. This high shear mixing and back up of materials led to aggregation of gluten (crosslinking), resulting in over torque of motor.

While the invention has been described in detail with respect to the specific embodiments thereof, it will be appreciated that those skilled in the art, upon attaining an understanding of the foregoing, may readily conceive of variations and equivalents to these embodiments. Accordingly, the scope of the present invention should be assessed as that of the appended claims and any equivalents thereto.

What is claimed is:

1. A melt-processed protein composition comprising:
    (a) at least one plant protein in an amount from about 20 to about 95 wt. %,
    (b) at least one plasticizer in an amount from about 20 to about 80 wt. % based on the weight of the protein, and
    (c) at least one electrophilic reagent in an amount from about 0.1 to about 20 wt. %, based on the weight of the protein,
    wherein the at least one electrophilic reagent is an olefinic or epoxide compound and contains less than 10 functional groups per molecule and has a molecular weight of from about 20 to about 1000 grams per mole, and
    wherein the melt-processed protein composition is produced by a method comprising blending the at least one plant protein, plasticizer and electrophilic reactant within a melt blending device at a temperature of from about 20 to about 100° C. and a shear rate of from about 1 to 100 Pascal-seconds.

2. The melt-processed composition of claim 1, wherein the plant protein is wheat gluten.

3. The melt-processed composition of claim 1, wherein the protein constitutes from about 40 wt % to about 80 wt. % of the composition, the plasticizer constitutes from about 40 wt % to about 60 wt. % based on the weight of the proteins, and the electrophilic reagent constitutes from about 2 wt. % to about 12 wt. % based on the weight of the proteins.

4. The melt-processed composition of claim 1, wherein the electrophilic reagent is an olefinic compound.

5. The melt-processed composition of claim 1, wherein the electrophilic reagent is an epoxide compound.

6. The melt-processed composition of claim 1, wherein the plasticizer is a polyhydric alcohol.

7. The melt-processed composition of claim 1, wherein the composition further comprises a starch polymer, reducing agent, antioxidant, dispersion aid, or a combination thereof.

8. The melt-processed composition of claim 1, wherein the composition is generally free of solvents.

9. The melt-processed composition of claim 1, wherein the composition further comprises an antimicrobially-active botanical oil.

10. A wipe comprising the melt-processed composition of claim 9.

* * * * *